(12) United States Patent
Daraio et al.

(10) Patent No.: US 8,720,250 B2
(45) Date of Patent: May 13, 2014

(54) SYSTEMS AND METHODS FOR CONTROLLING HIGHLY NONLINEAR ACOUSTIC WAVES OR PULSES

(75) Inventors: Chiara Daraio, Pasadena, CA (US); Alessandro Spadoni, Lausanne (CH); Tian Lan, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 230 days.

(21) Appl. No.: 13/035,681

(22) Filed: Feb. 25, 2011

(65) Prior Publication Data

US 2011/0209940 A1 Sep. 1, 2011

Related U.S. Application Data

(60) Provisional application No. 61/308,797, filed on Feb. 26, 2010.

(51) Int. Cl.
 - *G01N 3/303* (2006.01)
 - *G01N 3/30* (2006.01)
 - *G01N 3/34* (2006.01)
 - *G01N 3/32* (2006.01)

(52) U.S. Cl.
 CPC ............... *G01N 3/30* (2013.01); *G01N 3/303* (2013.01); *G01N 3/34* (2013.01); *G01N 3/32* (2013.01)
 USPC .......................... 73/12.11; 73/12.04; 73/12.05

(58) Field of Classification Search
 CPC ........... G01N 3/30; G01N 3/303; G01N 3/34; G01N 3/32
 USPC ............ 73/11.01, 11.02, 12.01, 12.02, 12.04, 73/12.05, 12.06, 12.11, 12.13, 12.14
 See application file for complete search history.

(56) References Cited

U.S. PATENT DOCUMENTS

| 4,893,624 A | 1/1990 | Lele |
| 5,736,642 A | 4/1998 | Yost et al. |
| 2006/0225509 A1 | 10/2006 | Haupt et al. |
| 2009/0204344 A1* | 8/2009 | Daraio et al. ............... 702/39 |
| 2009/0229910 A1 | 9/2009 | Daraio |

FOREIGN PATENT DOCUMENTS

| WO | WO 2009100061 A2 * | 8/2009 |
| WO | WO 2009100064 A2 * | 8/2009 |

OTHER PUBLICATIONS

International Preliminary Report on Patentability issued by the IPEA/KR for PCT/US2011/026371 with a mailing date of May 24, 2012.

Johnson, P.A., et al., Physical Acoustics: Nonlinear Acoustics of Unconsolidated Granular Media I, J. Accoust. Soc. Am. 2008, 123: 3271-3272.

Ambati, M., et al., Surface Resonant States and Superlensing in Acoustic Metamaterials. 2007. *Physical Review B*. 75:195447-1-195447-5.

(Continued)

*Primary Examiner* — Peter Macchiarolo
*Assistant Examiner* — Rose M Miller
(74) *Attorney, Agent, or Firm* — Steinfl & Bruno LLP

(57) ABSTRACT

Systems and methods for creating sound bullets are described. Such sound bullets are created by controlling and/or redirecting highly nonlinear acoustic waves or pulses propagating through an array of actuators. The controlling and/or redirecting of the acoustic waves or pulses is achieved though methods such as applying pre-compressive forces to the array of actuators or by selection of size, shape and/or material of the actuators.

29 Claims, 18 Drawing Sheets

(56) References Cited

OTHER PUBLICATIONS

Buckingham, M., et al., Imaging the Ocean with Ambient Noise. 1992. *Nature.* 356:327-329.

Cain, C., et al., Concentric-Ring and Sector-Vortex Phased-Array Applicators for Ultrasound Hypothermia. 1986. *IEEE Trans on Microwave Theory and Technique.* 34(5): 542-551.

Carretero-Gonzalez, R., et al., Dissipative Solitary Waves in Periodic Granular Media. 2009. *Physical Review Letters*, 102, 024102.

Chatterjee, A., Asymptotic Solution for Solitary Waves in a Chain of Elastic Spheres. 1999. *Physical Review E.* 59(5): 5912-5919.

Clement, G.T., Perspectives in Clinical Uses of High-Intensity Focused Ultrasound. 2004. *Ultrasonics.* 42:1087-1093.

Coste, C., et al., On the Validity of Hertz Contact Law for Granular Material Acoustics. 1999. *Eur. Phys. J, B.* 7:155-168.

Coste C., et al., Solitary Waves in a Cahin of Beads under Hertz Contact. 1997. *Physical Review E.* 56(5):6104-6117.

Coste C., et al., Sound Propagation in a Constrained Lattice of Beads: High-Frequency Behavior and Dispersion Relation. 2008. *Physical Review E.* 77:021302-1-021302-13.

Daraio, C., et al., Strongly Nonlinear Waves in a Chain of Teflon Beads. 2005. *Physical Review E.* 72:016603-1-016603-9.

Daraio, C., et al., Tunability of Solitary Waves Properties in One-Dimensional Strongly Nonlinear Phononic Crystals. 2006. *Physical Review E.* 73:026610-1-026610-10.

Daraio C, et al., Energy Trapping and Shock Disintegration in a Composite Granular Medium. 2006. *Physical Review Letter.* 96: 058002-1-058002-4.

Daraio, C., et al., Pulse Mitigation by a Composite Discrete Medium. 2006. *J. Phys. IV France.* 134:473-479.

Daraio, C., et al., Highly Nonlinear Contact Interaction and Dynamic Energy Dissipation by Forest of Carbon Nanotubes. 2004. *Applied Physics Letter.* 85(23):5724-5726.

Daraio, C., et al., Strongly Nonlinear Waves in 3D Phononic Crystals. 2004. *AIP Conf Proc.* 706:197-200.

Daraio, C., et al Impact Response by a Foamlike Forest of Coiled Carbon Nanotubes. 2006, *J. Appl. Phys.* 100: 064309-1-064309-4.

Daraio, C., et al., Dynamic Nanofragmentation of Carbon Nanotubes. 2004, *Nano Letters.* 4(10):1915-1918.

Daraio, C., et al., Strongly Nonlinear Waves in Polymer Based Phononic Crystals. 2005, *Shock Compression of Condensed Matter*, pp. 1507-1510.

Daraio, C., et al., Strongly Nonlinear Waves in Dynamics in a Chain of Polymer Coated Beads. 2006, *Physical Review E.* 73:026612-1-026612-7.

Daraio, C., et al., Propagation of Highly Nonlinear Signals in a Two Dimensional Network of Granular Chains. 2007, *Shock Compression of Condensed Matter.* 1419-1422.

Daraio, C., et al Method and Device for Actuating and Sensing Highly Nonlinear Solitary Waves in Surfaces, *Structures and Materials*, 2011, University of Pittsburg.

Davis, J.L., Wave Propagation in Solids and Fluids. 1998, Springer-Verlag, New York. 500-501.

Dickson J. A., et al., In vivo Hyperthermia of Yoshida Tumor Induces Entry of Non-Poliferating Cells into Cycle. 1976, *Nature*, 263: 773-774.

Doney, R., et al., Decorated, Tapered. And Highly Nonlinear Granular Chain. 2006, *Physical Review Letters*, 97: 155502-1-155502-4.

Doney, R., et al., Impulse Absorption by Tapered Horizontal Alignments of Elastic Spheres. 2005, *Physical Review E.* 72: 041304-1-041304-11.

Ebbini E., et al., Multiple-Focus Ultrasound Phased-Array Pattern Synthesis: Optimal Driving-Signal Distributions for Hyperthermia. 1989, *IEEE Transactions on Ultrasonics, Ferroelectrics and Frequency Control*, 36(5): 540-548.

Fatemi, M., et al., Ultrasound-Simulated Vibro-Acoustic Spectrography, 1998, *Science*, 280:82-85.

Fink, M., Time Reversal of Ultrasonic Fields-Part I Basic Principles. 1992, *IEEE Transactions on Ultrasonics, Ferroelectrics, and Frequency Control*, 39(5): 555-566.

Fok, L., et al., Acoustic Metamaterials. 2008, *MRS Bulletin*, 33:931-934.

Fraternali, F., et al., Optimal Design of Composite Granular Protectors. 2010, *Mechanics of Advanced Materials and Structures*, 17:1-19.

Haar, T., Ultrasound Focal Beam Surgery. 1995, *Ultrasound in Med. & Biol.* 21(9): 1089-1100.

Hakensson, A., et al., Acoustic Lens Design by Genetic Algorithms. 2004, *Physical Review B.* 70:214302-1-214302-9.

Hakensson, A., et al., Sound Focusing by Flat Acoustic Lenses Without Negative Refraction. 2005, *Applied Physics Letters.* 86:054102-1-054102-3.

Hecht, E., Optics, 4th Edition. Pearson Addison Wesley, Spring 2008, 2 pages total.

Herbold, E., et al., Solitary and Shock Waves in Discrete Strongly Nonlinear Double Power-Law Materials. 2007, *Appl. Phys. Lett.* 90:261902-1-261902-3.

Herbold, E., et al., Pulse Propagation in Linear and Nonlinear Diatomic Periodic Chain: Effects of Acoustic Frequency Band Gap. 2009, *Acta Mech.* 205:85-103.

Herbold, E., et al., Shock Wave Structure in a Strongly Nonlinear Lattice With Viscous Dissipation. 2007, *Physical Review E.* 75:021304-1-021304-8.

Herbold, E., et al., Tunable Frequency Band-Gap and Pulse Propagation in a Strongly Nonlinear Diatomic Chain. 2009, *Acta Mechanica*, 205, 1-4, 85-103.

Hong, J., et al., Solitary Waves in the Granular Chain. 2007, *Physics Report*, pp. 1-46.

Hong, J., Universal Power-Law Decay of the Impulse Energy in Granular Protectors. 2005, *Physical Review Letters.* 94:108001-1-108001-4.

Hong, J., et al., Characterization of Soliton Damping in the Granular Chain Under Gravity, 2000, *Physical Review E.* 61(1): 964-967.

Hong, J., Nondestructive Identification of Impurities in Granular Medium. 2002, *Appl. Phys. Lett.* 81:4868-4870.

Dhawan, A.P. et al., Chapter 1: Intro to Medical Imaging and Image Analysis: A Multidisciplinary paradigm, *Principles and Advanced Methods in Medical Imaging and Image Analysis* by World Scientific Publishing Co. Pte. Ltd., 2008, pp. 1-8.

Job, S., et al., How Hertzian Solitary Waves Interact With Boundaries in a 1D Granular Medium. 2005, *Phy. Rev. Lett.* 94:178002-1-178002-4.

Job, S., et al., Solitary Wave Trains in Granular Chains: Experiments, Theory and Simulations. 2007, *Granular Matter*, 10:13-20.

Johnson, K.L. Contact Mechanics, Cambridge University Press, 1985, pp. 1-17.

Khatri, D., et al., "Highly nonlinear waves' sensor technology for highway infrastructures", *Proc. SPIE* 6934, Nondestructive Characterization for Composite Materials, Aerospace Engineering, Civil Infrastructure, and Homeland Security 2008, 69340U (Apr. 8, 2008).

Korteweg, et al., On the change of form of long waves advancing in a rectangular canal, and on a new type of long stationary waves, *Phil. Mag.* 1895, vol. 5, No. 39, pp. 422-443.

Krim, H., et al., Two Decades of Array Signal Processing Research. 1996, *IEEE Signal Processing Magazine*, 67-94.

Kushibiki, J., et al., Material Characterization by Line-Focus-Beam Acoustic Microscope. 1985, *IEEE Transactions on Sonics and Ultrasonics*, SU-32(3):189-212.

Lalonde, R.J., et al., Field Conjugate Acoustic Lenses for Ultrasound Hyperthermia. 1991, *Ultrasonics Symposium.* 1339-1342.

Lalonde, R. J., et al Variable Frequency Field Conjugate Lenses for Ultrasound Hyperthermia. 1995, *IEEE Trans on Ultra, Ferro, Freq.* 42(5): 825-831.

Li, J., et al., Experimental Demonstration of an Acoustic Magnifying Hyperlens. 2009, *Nature Materials*, 931-934.

Manciu, F., et al., Secondary Solitary Wave Formation in Systems With Generalized Hertz Interactions. 2002, *Phys Rev E.* 66:016616-1-016616-11.

Manciu, M., et al., Dynamics of a Gravitationally Loaded Chain of Elastic Beads. 2000, *Choas.* 10(3):658-669.

Porter, M., et al Highly Nonlinear Solitary Waves in Heterogeneous Periodic Granular Media. 2009, *Physica D.* 238:666-676.

(56) References Cited

OTHER PUBLICATIONS

Nesterenko, V. F., et al., Anomalous Wave Reflection at the Interface of Two Strongly Nonlinear Granular Media. 2005, *Physical Review Letters*. 95:158702-1-158702-4.

Nesterenko, V. F., et al., Architectural Acoustics: Acoustics of Concert Halls II. 2008, *J. Acoust. Soc. Am.* 123(5): 265 Pages.

Nesterenko, V. F., Nonlinear Impulses in Particulate Materials, High Pressure Shock Compression of Condensed Matter, *Dynamics of Heterogeneous Materials*, Springer New York, 2001, pp. 1-136.

Nesterenko, V. F., Propagation of Nonlinear Compression Pulses in Granular Media. 1984, *Journal of Applied Mechanics and Technical Physics*. 733-743.

Ocheltree, K., et al., An Ultrasonic Phased Array Applicator for Hyperthermia. 1984, *IEEE Trans on Sonics and Ultrasonics*. SU-31(5): 526-531.

Olson, H., Elements of Acoustical Engineering. 1940, D. Yan Nostrand Company Inc. 344 pages.

Porter, M., et al., Highly Nonlinear Solitary Waves in Periodic Dimer Granular Chains. 2008, *Physical Review E*. 77:015601-1-015601-4.

Rosas, A., Observation of Two-Wave Structure in Strongly Nonlinear Dissipative Granular Chains. 2007,*Phys. Rev. Lett.* 98:164301-1-164301-4.

Rosas, A., et al., Pulse Propagation in Chains with Nonlinear Interactions. 2004, *Phys Rev E*. 69:016615-1-016615-4.

Sadd, M., et al., Contact Law Effects on Wave Propagation. 1993, *Int. J. Non-linear Mechanics*. 28(2): 251-265.

Sen, S., et al., Impulse Backscattering Based Detection and Imaging of Shallow Buried Objects. 2003, *Mat. Res. Soc. Symp Proc.* 759:MM2.9.1-MM2.9.8.

Shellman, Y., et al., Hyperthermia Induces Endoplasmic Reticulum-Mediated Apoptosis. 2008, *Journal of Investigative Dermatology*. 128: 949-956.

Shukla, A., et al., Influence of Loading Pulse Duration on Dynamic Load Transfer in a Simulated Granular Medium. 1993, *J. Mech. Phys. Solids* 41(11):1795-1808.

Sillerberg, Y., Collapse of Optical Pulses. 1990, *Optics Letters*. 15(22): 1282-1284.

Sokolow, A., et al., Solitary Wave Train Formation in Hertzian Chains. 2007, *EPL*. 77:240021-24002-4.

Sukhovich, A., et al., Negative Refraction and focusing of Ultrasound in 2D Phononic Crystals. 2008,*Phys. Rev. B*. 77:014301-1-014301-9.

Tumbull, D., et al., Beam Steering with Pulsed Two-Dimensional Transducer Arrays. 1991, *IEEE Trans Ultra, Ferro, Freq*. 38(4): 320-333.

Vaezy, S., et al., Image-Guided Acoustic Therapy. 2001, *Annu Rev Biomed Eng*. 3:375-390.

Van Trees, H., et al., Optimum Array Processing. 2002.

Van Veen, B., et al., Beamforming: A Versatile Approach to Spatial Filtering. 1988, *IEE ASSP Magazine*. 4-24.

Yang, S., Focusing of Sound in 3D Phononic Crystal. 2004,*Phys. Rev Lett*. 93(2): 024301-1024301-4.

Zhang, X., et al., Superlenses to Overcome the Diffraction Limit. 2008, *Nature Materials*. 7:435-441.

Zhu, Y., et al., Propagation of Explosive Pulses in Assemblies of Disks and Spheres. 1997, *J. of Engineering Mechanics*, pp. 1050-1059.

Holt, R. G., et al. Bubbles and HIFU: the good, the bad and the ugly, in Andrew, M. A, Crum, L. A, Vaezy. S, Proceedings of the 2nd International Symposium on Therapeutic Ultrasound, 2002, pp. 120-131.

Ponomarenko, A., et al.., Linear optical bullets, *Optics Communication* 2006, 261: 1-4.

Rizzo, P., et al., Load Measurement and Health Monitoring in Cable Stays via Guided Wave Magnetostrictive Ultrasonics, *Materials Evakuations* 2004, 1057-1065.

\* cited by examiner

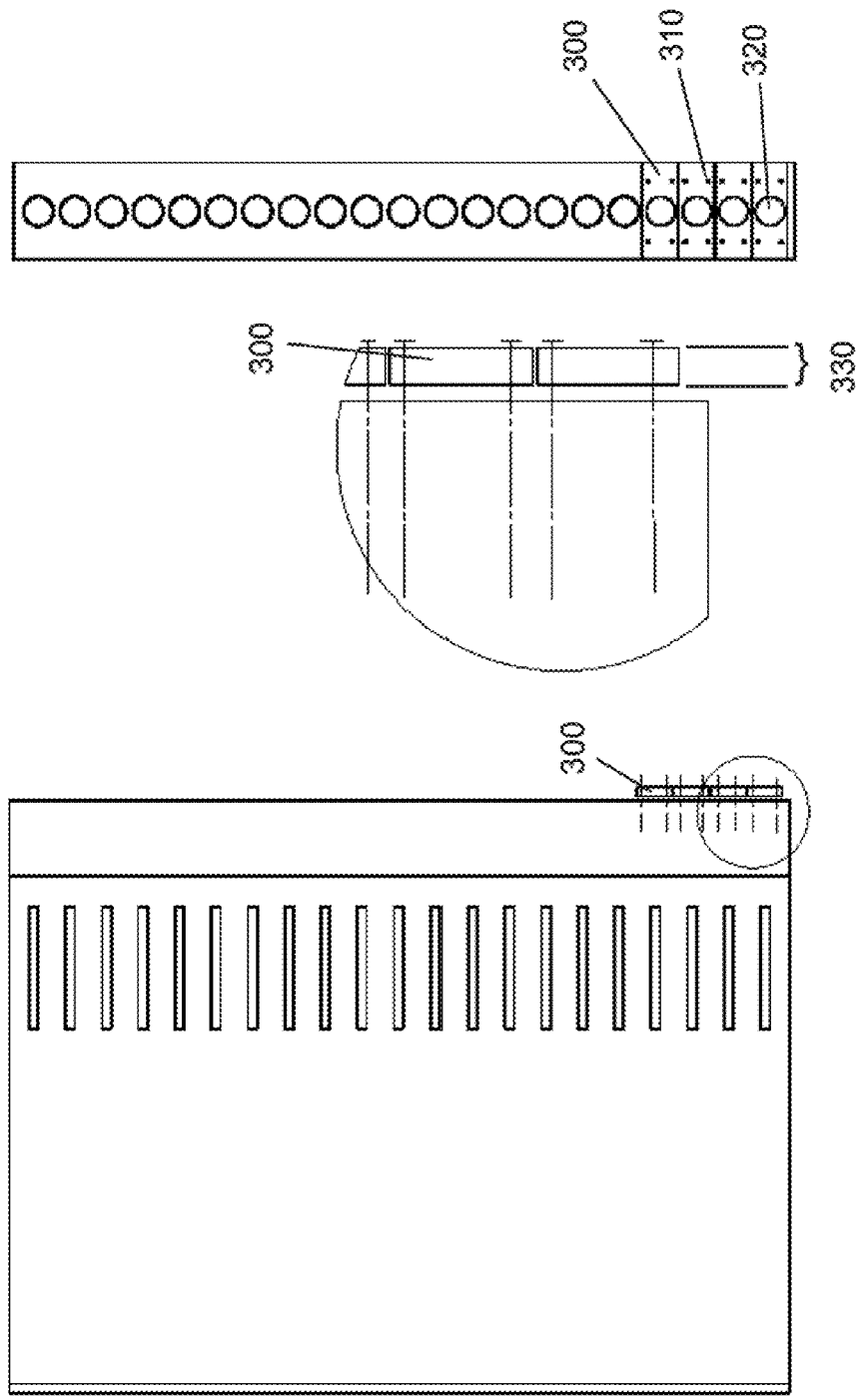

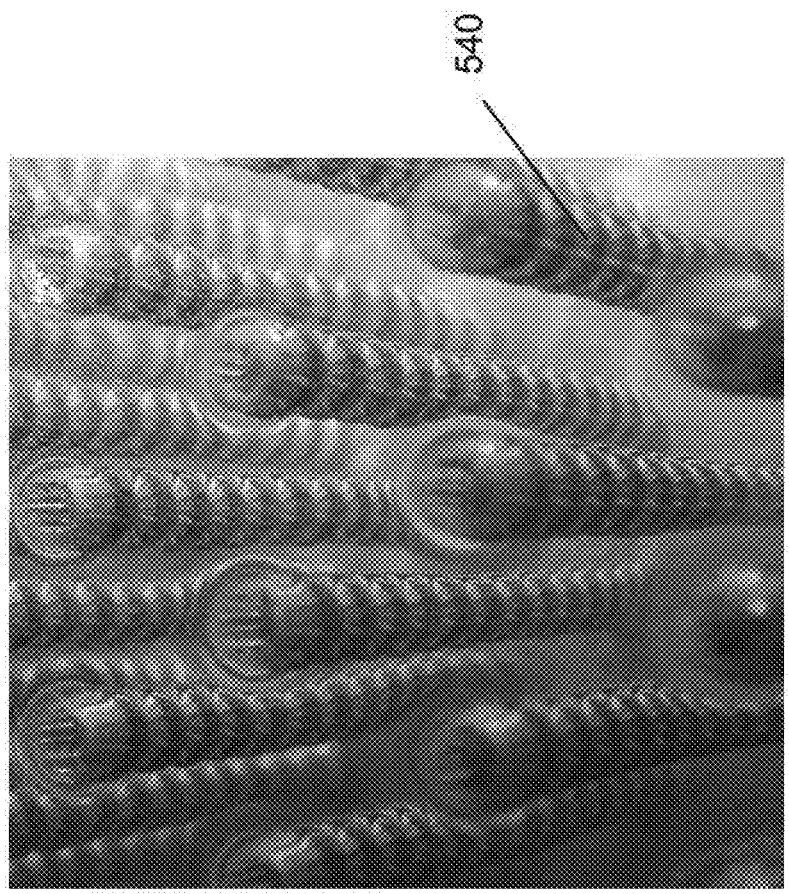

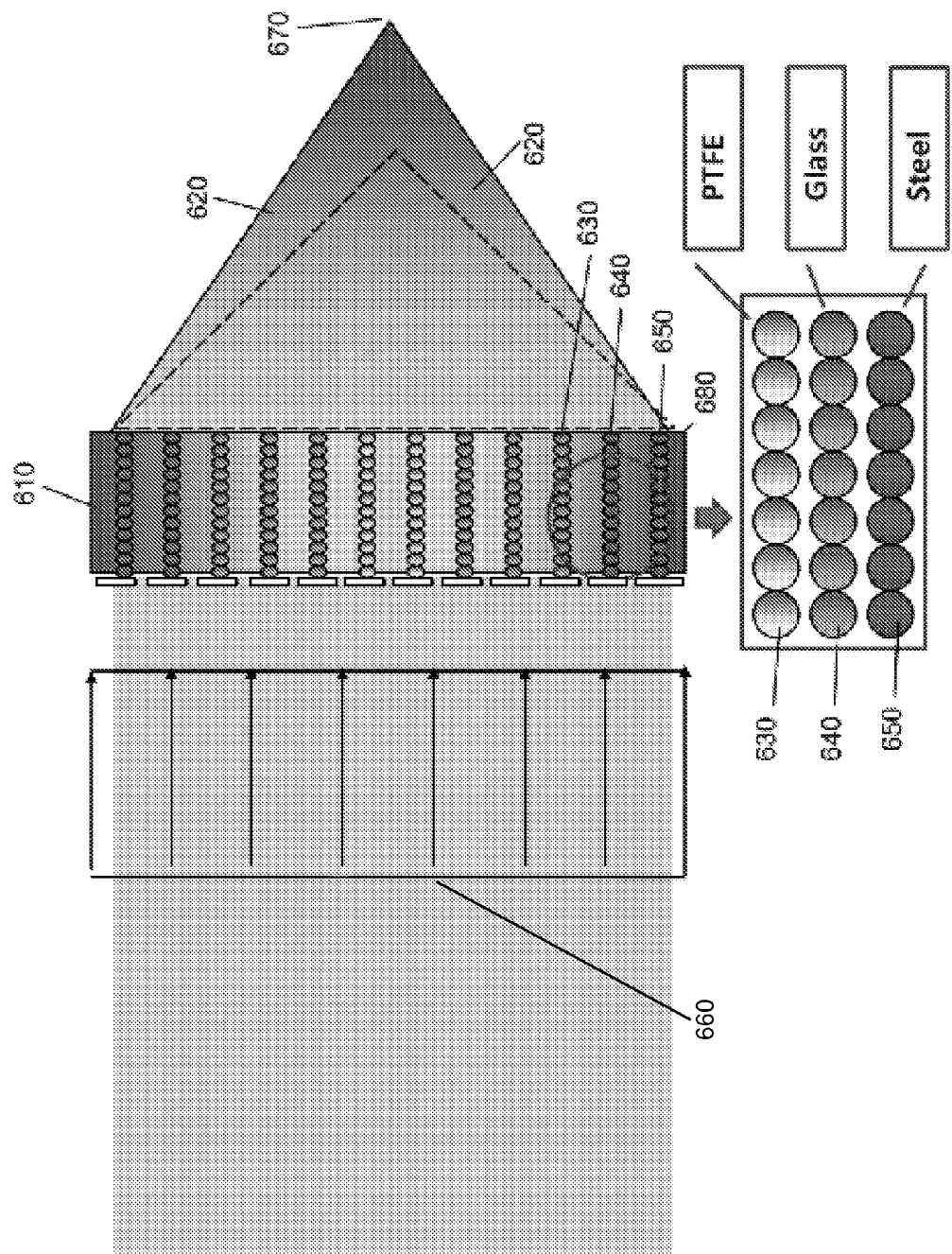

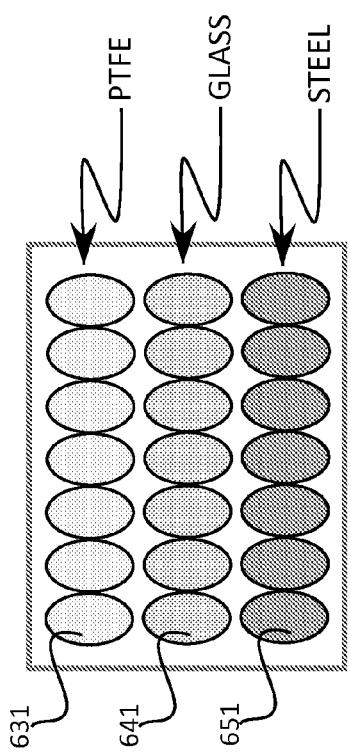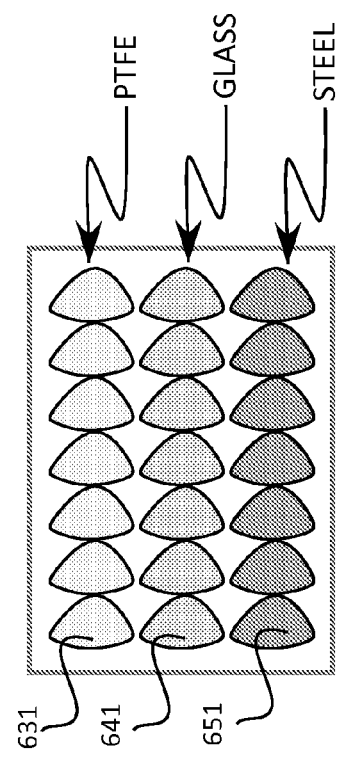

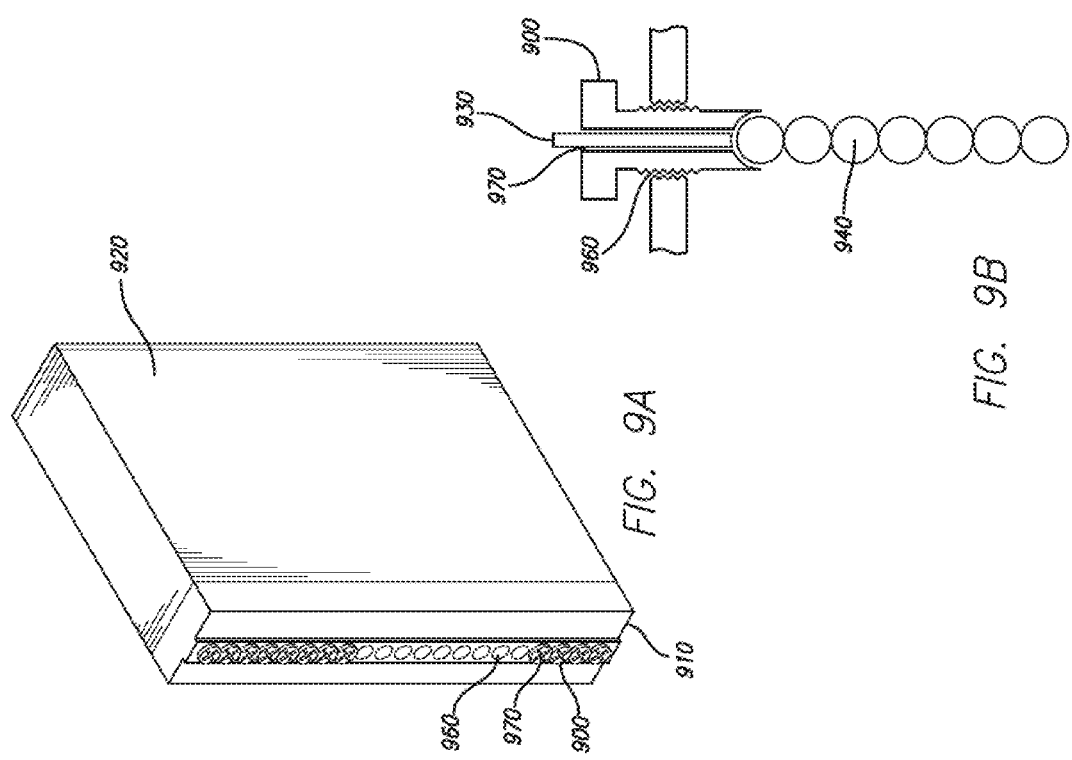

SYSTEMS AND METHODS FOR CONTROLLING HIGHLY NONLINEAR ACOUSTIC WAVES OR PULSES

CROSS REFERENCE TO RELATED APPLICATIONS

The present application claims priority to U.S. Provisional Application No. 61/308,797, filed on Feb. 26, 2010, which is incorporated herein by reference in its entirety.

STATEMENT OF GOVERNMENT GRANT

This invention was made with government support under Grant No. DMR0520565 awarded by the National Science Foundation. The government has certain rights in the invention.

FIELD

The present disclosure relates to focusing acoustic waves or pulses. Moreover, it relates to systems and methods for controlling highly nonlinear acoustic waves or pulses.

BACKGROUND

A model typically used to represent simplest forms of granular systems consisted of a one dimensional chain of spherical beads regulated by Hertzian contact interaction potentials. However, a general wave dynamic theory supporting compact solitary waves was derived for structured homogeneous materials showing a highly nonlinear force (F)-displacement ($\delta$) response dictated by the intrinsically nonlinear potential of interaction between its fundamental components. This general nonlinear spring-type contact relation can be expressed as:

$$F \approx A\delta^n, \qquad (1)$$

where n is a nonlinear exponent of the contact interaction (n>1) of a fundamental component and A is parameter for the material. For Hertzian systems, such as those consisting of a chain of spherical beads, the n exponent of interaction is equal to 1.5.

Within the present disclosure, "granular matter" is defined as an aggregate of "particles" in elastic contact with each other, preferably in linear or network shaped arrangements. In addition to the nonlinear contact interaction and the particle's geometry, another unique feature of the granular state is provided by a so-called zero tensile strength, which introduces additional nonlinearity (asymmetric potential) to the overall response. Consequently, in the absence of static pre-compression on the system, the linear range becomes negligible in the interaction of forces between neighboring particles, thus leading to materials with a characteristic sound speed equal to zero in its uncompressed state ($c_0=0$), known as a "sonic vacuum". This highly nonlinear wave theory supports, in particular, a new type of compact highly tunable solitary waves that have been experimentally and numerically observed in several works for the case of one-dimensional Hertzian granular systems.

SUMMARY

According to a first aspect, a system for controlling and/or redirecting acoustic waves or pulses is described, the system comprising: a two-dimensional or three-dimensional array of rows of actuators, each row comprising a plurality of independently tuned highly nonlinear actuators, the actuators being made of different materials such that a first row of the array of actuators is made of a first material and at least a second row of the array of actuators is made of a second material different from the first material.

According a second aspect, a system for controlling and/or redirecting acoustic waves or pulses is described, the system comprising: a two-dimensional or three-dimensional array of rows of actuators, each row comprising a plurality of independently tuned highly nonlinear actuators; and a plurality of regulator screws, each regulator screw associated with a first end of a respective row of actuators, the plurality of regulator screws configured to controllably pre-compress each respective row of actuators to which the regulator screws are connected with, such that a first row of the actuators is pre-compressed to a compression different from the compression of at least one other row of the actuators.

According to a third aspect, a system for controlling and/or redirecting acoustic waves or pulses is described, the system comprising: a two-dimensional or three-dimensional array of rows of actuators, each row comprising a plurality of independently tuned highly nonlinear actuators; and a plurality of hinged levers, each hinged lever connected with a first end of a respective row of actuators.

According to a fourth aspect, a system for controlling and/or redirecting acoustic waves or pulses is described, the system comprising: a two-dimensional or three-dimensional array of rows of actuators, each row comprising a plurality of independently tuned highly nonlinear actuators; and a plurality of micro- or nano-positioning devices, each micro- or nano-positioning device connected with a first end of a respective row of actuators.

According to a fifth aspect, a method of controlling and/or redirecting acoustic waves or pulses is described, the method comprising: providing a two-dimensional or three-dimensional array of rows of actuators, each row comprising a plurality of independently tuned highly nonlinear actuators; providing a plurality of regulator screws, each regulator screw associated with a first end of a respective row of actuators; and pre-compressing each row of the actuators such that a first row of the actuators is pre-compressed to a compression different from at least one other row of the actuators, the pre-compressing being performed by screwing in or screwing out the plurality of the regulator screws, wherein differences in compression of each of the rows of actuators control and/or redirect the acoustic waves or pulses.

According to a sixth aspect, a method of controlling and/or redirecting acoustic waves or pulses is described, the method comprising: providing a two-dimensional or three-dimensional array of rows of actuators, each row comprising a plurality of independently tuned highly nonlinear actuators; providing a plurality of hinged levers, each hinged lever connected with a first end of a respective row of actuators; and pre-compressing each row of the actuators such that a first row of the actuators is pre-compressed with the hinged lever to a compression different from at least one other row of the actuators, wherein differences in compression of each of the rows of actuators control and/or redirect the acoustic waves or pulses.

According to a seventh aspect, a method of controlling and/or redirecting acoustic waves or pulses, the method comprising: providing the system according to the fourth aspect; and pre-compressing each row of the actuators with the piezo-electric devices, applying compressive forces controlled by a motor controller, such that the first row of the actuators is pre-compressed to a compression different from at least one other row of the actuators, wherein differences in compression of each of the rows of actuators control and/or redirect the acoustic waves or pulses.

According to an eighth aspect, a method of controlling and/or redirection acoustic waves or pulses, the method comprising: providing a two-dimensional or three-dimensional array of rows of actuators, each row comprising a plurality of independently tuned highly nonlinear actuators; and providing acoustic waves or pulses to a first end of the rows of the actuators, the input acoustic waves or pulses propagating to a first row of the actuators at a different time from the acoustic waves or pulses propagating to at least one other row of the actuators, thereby controlling and/or redirecting the acoustic waves or pulses exiting from a second end of the rows of the actuators.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

FIGS. 3A-3C show schematic diagrams of various views of the exemplary two-dimensional system for controlling and/or redirecting acoustic waves or pulses, wherein plates and screws are used to contain actuators in the system.

FIG. 5 shows an arrangement of a three-dimensional array of actuators in a polymer matrix.

FIG. 9A shows an exemplary two- or three-dimensional system for controlling and/or redirecting acoustic waves or pulses, wherein regulator screws are used to apply the pre-compression.

FIG. 9B shows a close-up cross-sectional view of a row of actuators with a regulator screw to apply the pre-compression.

DETAILED DESCRIPTION

Figure 1:
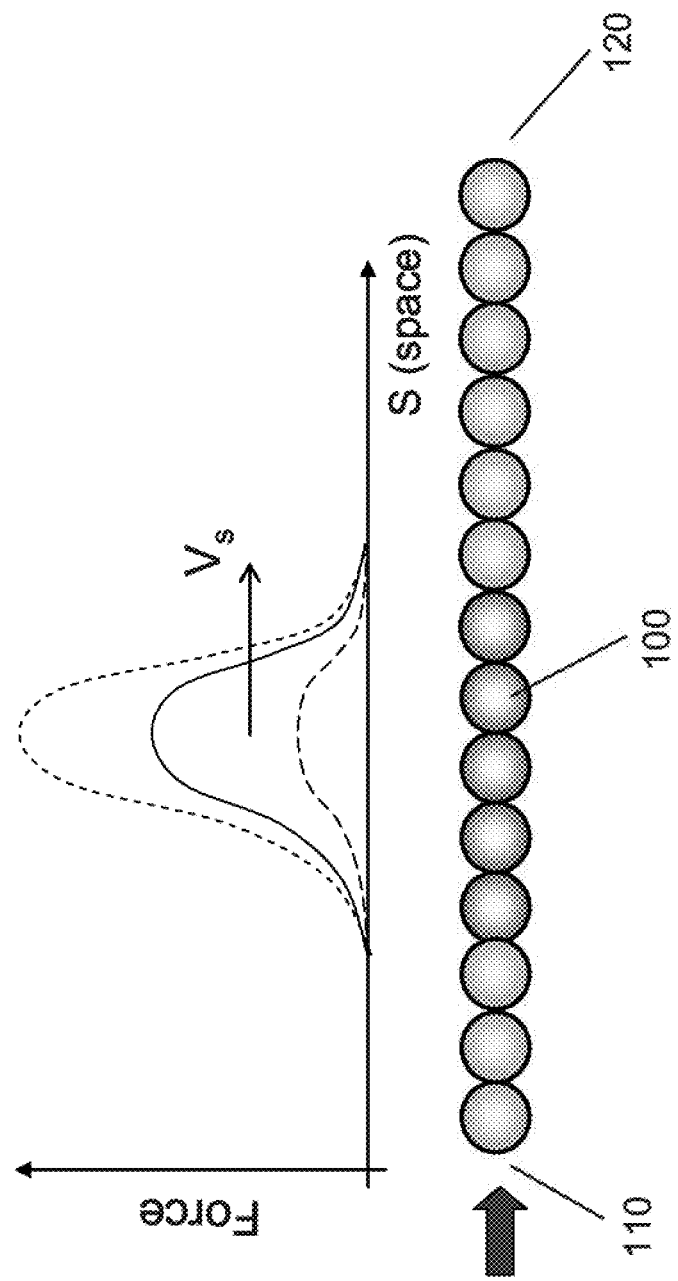
FIG. 1 shows a one-dimensional schematic diagram of a chain of actuators and its highly nonlinear solitary waveform.

A broad variety of applications can potentially benefit from development of systems and methods to perform accurate acoustic wave control, channeling and redirection. By way of example and not of limitation, such systems can be used in marine detection/communication, nondestructive testing and structural health monitoring, seismic sensing and microscopy and medical surgery (reference [2]). The methods used to focus/defocus and redirect sound include, but are not limited to geometrical focusing, constructive phase lags and inverse methods [3-9].

One known applications based on acoustic wave control is acoustic imaging/visualization as described in reference [2]. The most common technique used to "visualize" sound is in a way that may be analogous to that used by an optical camera. That is, by focusing scattered sound energy on an acoustic receptor. Another way, as in the case of sonar, is based on pulse-echo method, in which an acoustic beam or a spherical wave is excited and backward scattered waves encountering objects lying in the path of the beam can be investigated. Acoustic tools, especially based on ultrasonic frequencies, have found broad applications in medical diagnosis and surgery. Ultrasound applications in medical surgery fall into two principal classes, diagnostic imaging and therapy, which differ in power, intensity, and duration of ultrasound (reference [10]).

Acoustic devices operating in the ultrasound regime may be employed both as detection and surgical devices. In the first case, the intensity of the emitted acoustic signals is low and reflections from soft tissue are reconstructed to obtain an image of the target of interest (reference [11]). In the second case, acoustic energy is employed to induce mechanical deformations of the tissue via thermal expansion in order to stimulate or accelerate normal physiological response to injury. High-intensity excitation, moreover, may be used to selectively destruct malign tissue by means of hyperthermia as described in reference [12]. It has long been known that, high-intensity focused ultrasound waves can kill tissue via coagulative necrosis. A simple way to generate high acoustic intensity is to use a single-element, geometrically induced transducer. Due to its small and fixed focal point, however, a mechanical scanning system was used in reference [3]. Electronic scanning phased arrays as described in references [4]-[5] are an attractive alternative, due to their fast scanning speed. In order to effectively control energy focusing, such systems have a large overall aperture and array theory requires that the spacing of array elements must be less than half a wavelength to avoid grating lobes (reference [6]). Also, by limiting beam steering to small angles, large numbers of transducer elements are applied in practical use.

By way of the pseudo-inverse, or field conjugation method as developed by Ebbini in reference [7], it is possible to design a phased array focusing without the help of electronic control or mechanical scanning. In this method, the designed acoustic focus is divided into a set of point foci of specified amplitude controlled by arrays of multiple transducer elements. Phased arrays are capable of modifying the shape and location of focal points. The same devices, in addition, can reduce or increase the focal volumes by combining multiple energy foci.

One example uses a field conjugate lens made of a plurality of elements through the device thickness to alter the field shape of a single transducer as described in references [8][9]. Phased array configurations provide tremendous flexibility in controlling the location and size of acoustic focal points and the arrays are composed of a large number of small elements.

The present disclosure describes arrays of highly nonlinear actuators for focusing, defocusing, redirecting and beam forming of acoustic waves. The present disclosure further describes methods to modify the wave shape and to generate tunable phase shifts in the actuators, thereby controlling the acoustic wave propagation. In addition, the high nonlinearity of the granular chains (actuators) composing the array allows for creation of high-intensity, compact acoustic pulses composed by only two fundamental harmonics as described in references [13][14].

Systems based on the selected spatial arrangements of granular particles for directional signal transmission or reception are inspired by beam-forming methods that are used for engineering and biomedical applications, as well as telecommunications and astronomy as in references [15][16]. In addition, the embodiments of the present disclosure describe intrinsic tunability of actuators for focal-point control and acoustic-beam positioning. Such tunability of the focal point can be achieved without need for spatial rearrangement of the arrays. By way of example and not of limitation, the following methods can be used to obtain the tunable focal point:

1) varying the mechanical properties of the particles in each chain in a controlled manner to achieve a desired velocity distribution in each chain
2) varying the non-uniform static pre-compression applied to the system
3) varying the impact velocity imparted by a mechanical striker on each individual chain
4) varying the size and/or shape (e.g., spherical, elliptical, conical) of the granular particles to change the velocity of the propagating wave or pulse FIG. 1 is a one-dimensional schematic diagram of a chain of actuators (100). The chain of actuators can be aligned in a straight line, for example, in a cylindrical guide. When an acoustic impact wave is introduced at first end (110), for example, by a striker, a highly nonlinear solitary wave with a finite wavelength is formed and propagated from the first end (110) to the second end (120). Regardless of the type or amplitude of the acoustic impact wave, the wave ultimately develops into a known sinusoidal shape with a defined profile and compact width (130). The one-dimensional array in the present disclosure is defined to be a single chain or row of actuators. The term "actuator" in the present disclosure intends to refer to any nonlinear material, capable of propagating the highly nonlinear acoustic wave. Examples of actuators can include, but are not limited to, granular particles and granular matter of various sizes and shapes. The term "first end" is defined as the side of the chain of actuators (or a system comprising chains of actuators) where the acoustic wave is introduced (e.g., inputted), and the term "second end" is defined as the side where the acoustic wave exits from the chain of actuators (or a system comprising chains of actuators).

A uniqueness of the dynamic response of the acoustic waves is derived from double nonlinearity: a highly nonlinear response in the contact interaction dynamics between the fundamental components (particles) and a zero tensile strength resulting in a negligible characteristic sound propagation (zero sound speed or sonic vacuum) in materials. An interesting property found in these systems appear when a material is under pre-compression (reference [18]), at an interface between two different granular systems (references [21][24]) or at an interface of granular media and solid matter (reference [20]) and in heterogeneous periodic structures (references [14][22]). A general wave equation for highly nonlinear systems can be derived from a general nonlinear contact interaction law (n≠1) between particles (reference [14]):

$$u_{\tau\tau} = u_x^{n-1} u_{xx} + G u_x^{n-3} u_{xx}^3 + H u_x^{n-2} u_{xx} u_{xxx} + I u_x^{n-1} u_{xxxx}, \quad (2)$$

where τ is a rescaled time, u is a displacement, and n is the nonlinear exponent from equation (1). Explicit expressions parameters I, H, G can be found in references [14][22]. The novelty and generality of the highly nonlinear wave equation is provided by also including linear and weakly nonlinear wave equations, and encompassing known limits (e.g., uniform chains). A closed form solution of equation (2) can also be obtained. In case of granular systems with no pre-compression, or weak pre-compression, a solution from direct integration is of the form:

$$u_\xi = v = B\cos^{\frac{2}{n-1}}(\beta\xi), \quad (3)$$

where ξ corresponds to a rescaled strain in the system, β scales with mass ratio of the particles, n is the exponent in equation (1), and B is a parameter dependent on the wave speed (Vs) and materials properties. If an initial pre-strain $\xi_0$ is approaches 0, the solitary hump in the waveform can be one hump of the periodic solution in equation (3) with a finite wavelength equal to only five particle diameters in the uniform case, and equal to π/β for heterogeneous periodic systems.

This solution demonstrates that in a highly nonlinear medium, two harmonics contribute to a stationary mode of propagation of the periodic signal. In analogy with the KdV solutions as described in reference [23], the highly nonlinear solitary waves are supersonic, thus their phase velocity is larger than the initial sound velocity ($c_0$) in the nonlinear medium, particularly in the case of an uncompressed system (e.g., $c_0$=0).

A unique feature of this waveform is the independence of the width with respect to the amplitude. Specifically, the spatial size of the wave is constant regardless of the amplitude or the speed of the wave. Such property is used as information carriers in signal transformation devices, allowing for confining dynamic excitations in crystals in quantized discrete stationary waves.

The speed of solitary wave $V_s$ derived from discretization of particles in a statically pre-compressed chain as a nonlinear function of the maximum dynamic force, is expressed as follows (reference [18]):

$$V_s = 0.9314 \left( \frac{4E^2 F_0}{a^2 \rho^3 (1-v^2)^2} \right)^{1/6} \frac{1}{(f_r^{2/3}-1)} \left\{ \frac{4}{15} [3 + 2f_r^{5/3} - 5f_r^{2/3}] \right\}^{1/2}, \quad (4)$$

where E is the Young's modulus, a is the particle's diameter and V is the Poisson ratio, ρ is the density, $F_0$ is the static pre-compression added to the system, and $f_r = F_m/F_0$ and $F_m$ is the maximum contact force between particles in a discrete chain. By changing the mechanical and/or the geometrical properties of the high nonlinear medium supporting the formation of highly nonlinear solitary waves, the shape and the speed of the traveling pulse can be tuned. Accordingly, the solitary waves in the highly nonlinear media can be engineered for specific applications as described, for example in references [1][17][19].

Figure 2:
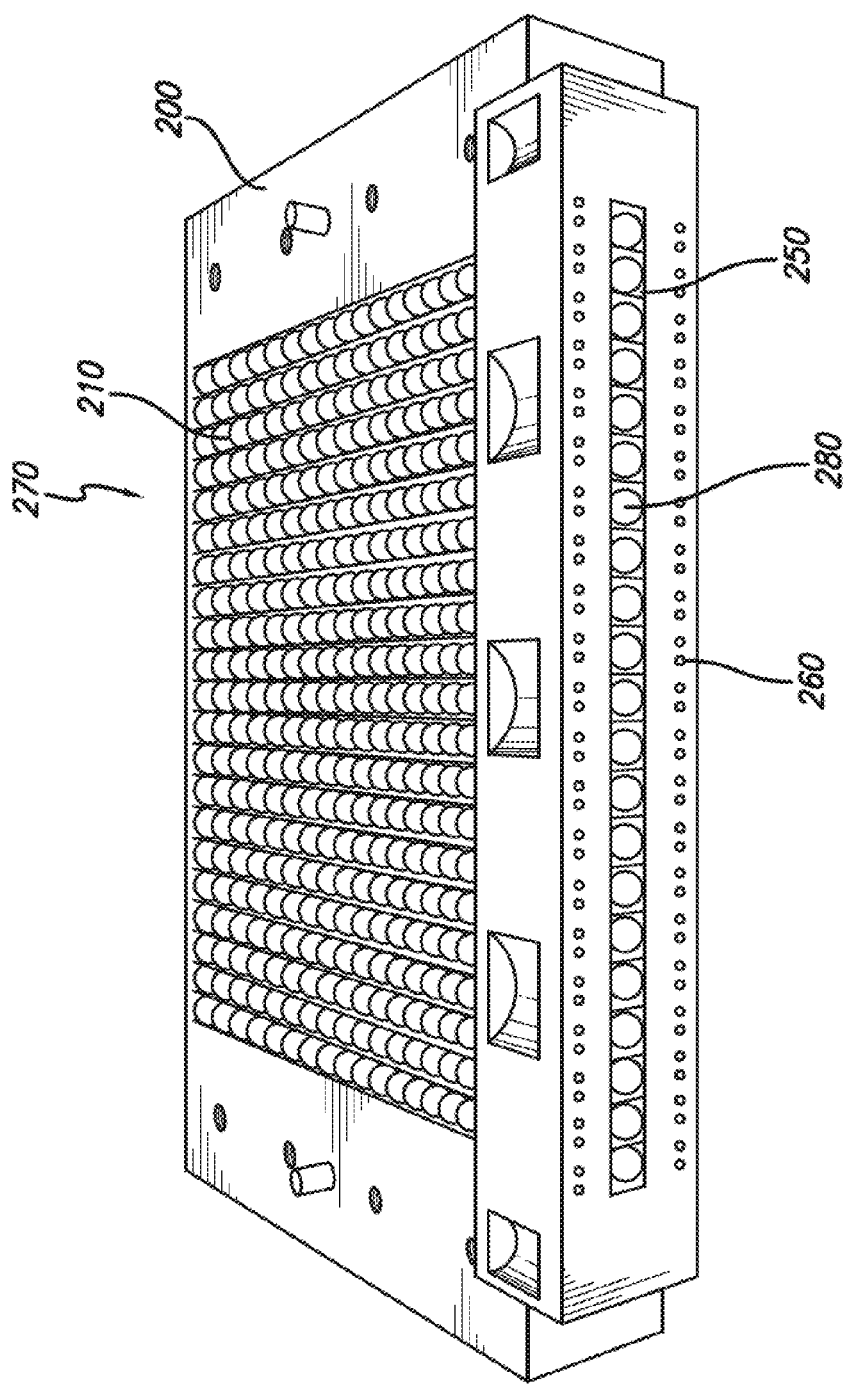
FIG. 2 shows an exemplary two-dimensional system for controlling and/or redirecting acoustic waves or pulses.

FIG. 2A shows an overview of an exemplary two-dimensional acoustic lens system (200) comprising an array (210) of actuators. The array of actuators (210) shown comprise a chain of stainless steel actuators (210) arranged in 21 rows of substantially straight lines in a rigid casing (200). Each row comprises 21 actuators and each row is separated by metal shim stocks (250) extending from a first end (270) of the actuators to a second end (280) of the actuators. The first end (270), as described in the present disclosure is intended to be a side of the system that is configured to receive acoustic impact wave, and the second end (280) is the side where the acoustic wave exits the system.

The metal shim stocks provide physical support for the chain of actuators to ensure desired alignment (e.g., straight line) such that when rotated, turned, and/or compressed, the actuators remain in place. Furthermore, the shims are made of material that is substantially softer than the actuators and are coated with non-stick material (e.g., TEFLON®) to minimize the effect of the acoustic waves being absorbed by the shim stocks. The second end (280) of each row of actuators can be configured to be covered with a plate (300), which can be held in place using a plurality of screws (310) as shown in FIG. 3A-3C to prevent the actuators from falling out. Screw holes (260) for the screws (310) are shown on the second end (280) of the system.

An impact wave is inputted to the actuators from the first end (270), causing the wave to propagate through the actuators, and ultimately exiting the actuators from the second end (280) of the system. The plates (300) comprise an opening (320) (e.g., slit, slot or hole) such that a target medium can be placed in direct contact with the actuators. The thickness (330) of the plates (300) can affect the ability for the propagating wave to pass through the plates (300). For example, if the thickness of the plates (300) is too large, then the acoustic waves can be absorbed and/or reflected by the plates, thus reducing the magnitude of the waves that actually pass through the openings (320) of the plates (300). However, if the plates (300) are too thin, then the actuators can break through the plates (300) if pressure is applied to the actuators. Although the plates (300) in the present disclosure show four screws and four screw holes per plate, more or less screws can be used to hold the plates (300) in place.

Figure 4A:
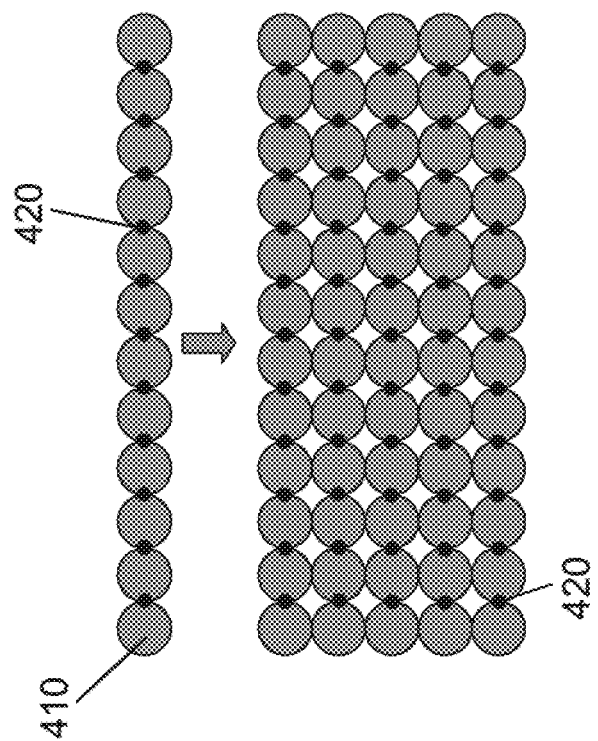
FIGS. 4A-4B show schematic diagrams of actuators welded and molded together.
Figure 4B:
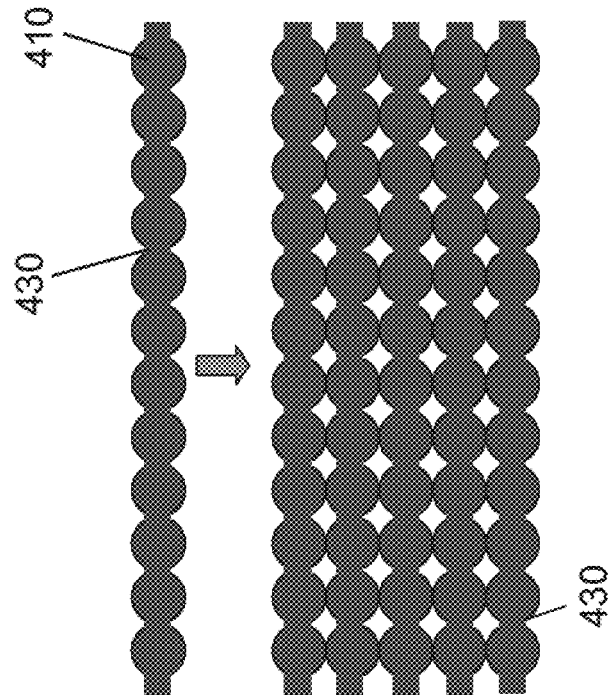

FIGS. 4A and 4B show schematic cross sectional views of techniques to assemble the two- or three-dimensional array of rows of actuators. According to a first technique, shown in FIG. 4A, the rows (410) are assembled with spot welded two-dimensional layers of packed grains, where the welded spots are indicated as (420). By spot welding the actuators, additional use of polymers for physical support can be avoided, which can be potential sources of acoustic wave dissipation. According to a second technique, shown in FIG. 4B, the rows are assembled molding each layer (430) separately.

FIG. 5 is an alternative arrangement of the array of actuators shown by a detailed example of a three-dimensional array of actuators embedded in a soft polymer matrix. By way of example and not of limitation, the actuators (540) shown are approximately 1 mm in diameter. However, those skilled in the art would understand that actuators of other sizes can instead be used. A choice of soft matrix with low friction enables the acoustic information to travel preferentially through the stiffer chains and provides structural support for the actuators.

Figure 6A:
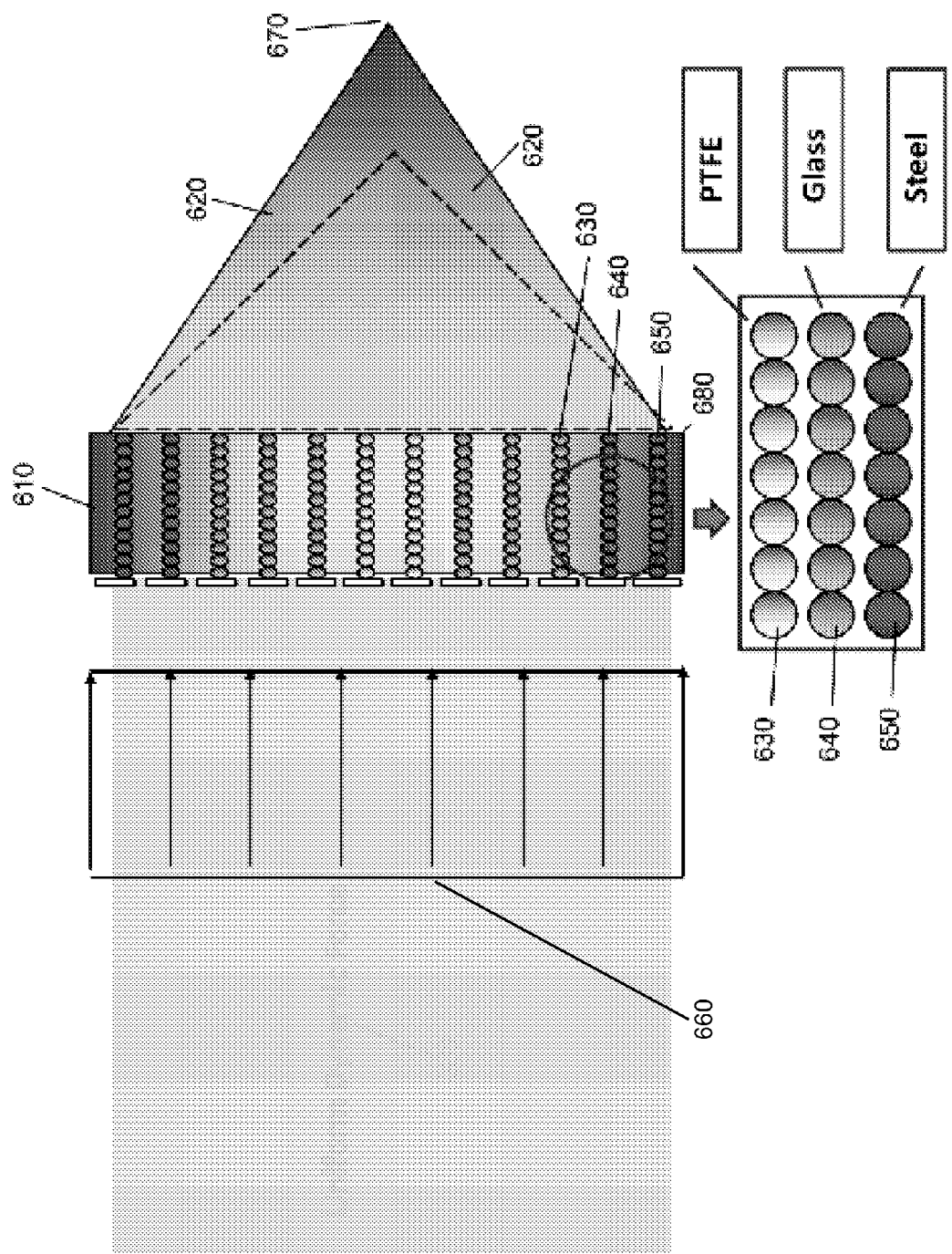
FIG. 6A shows an exemplary two- or three-dimensional system for controlling and/or redirecting acoustic waves or pulses wherein the actuators comprises different materials.
Figure 6B:
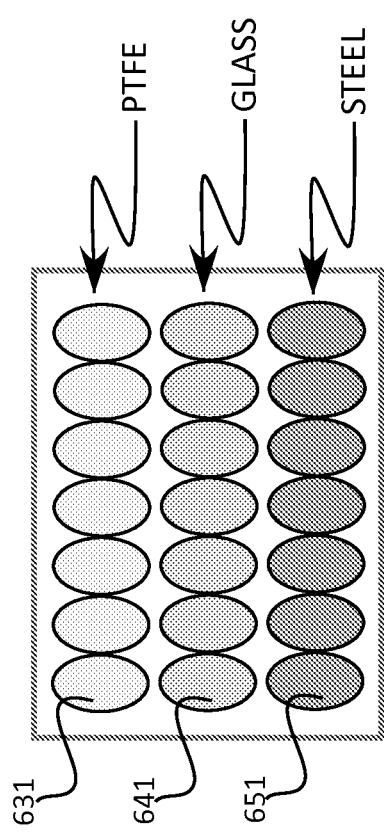
FIG. 6B shows the inset of FIG. 6A with elliptical particles.
Figure 6C:
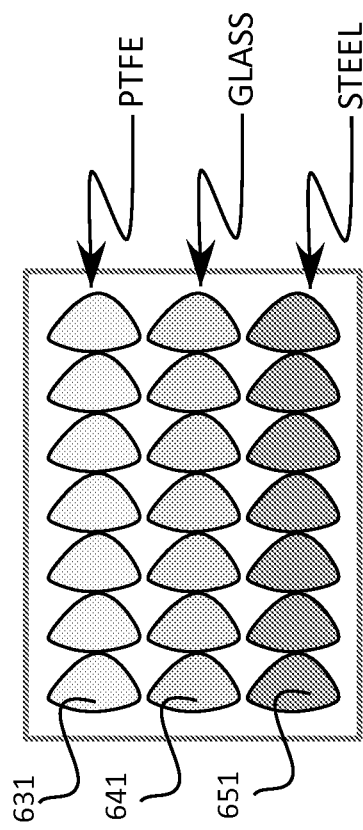
FIG. 6C shows the inset of FIG. 6A with conical particles.

FIG. 6A shows an embodiment of a system for controlling and/or redirecting acoustic waves or pulses according to the present disclosure, where a two- or three-dimensional array (610) of rows is shown in cross section. In accordance with such embodiment, control and/or redirection (620) of acoustic waves is achieved by providing the array (610) with particles assembled from different materials, where a first row (630) of the array of actuators is made of a first material and at least one second row (640, 650) of the array of actuators is made of a second material different from the first material. By way of example, the inset of FIG. 6A shows an enlargement of the last three rows (630, 640, 650), made of PTFE (630), glass (640) and steel (650), respectively. FIG. 6B shows the inset of FIG. 6A with elliptical particles made of PTFE (631), glass (641) and steel (651). FIG. 6C shows the inset of FIG. 6A with conical particles made of PTFE (632), glass (642) and steel (652). Although only PTFE, glass and steel are shown, any solid material from a periodic table can be used. Other examples include rubber, brass, bronze, ceramic materials, and any other metals or alloys thereof.

The system of FIG. 6A is subject to a uniform dynamic force acoustic impact wave (660). Control and/or redirection (620) of the force (660) is achieved through the different properties of the various materials adopted. For example, a material such as steel (650) has a higher Young's modulus than that of glass (640). Thus, the acoustic wave propagates through the steel at a higher velocity than through the glass. By selectively choosing the material of the actuators, the acoustic wave exiting from the second end (680) of the acoustic lens system (610) can be redirected such that the output waves from each row converges (thereby focusing) at a particular point (670). Thus, the concentrated, focused acoustic wave will be referred to as a 'sound bullet' herein in the present disclosure. The resolution of the sound bullet at the focal point (670) can be improved by selecting the material of the actuators where the Young's modulus varies gradually from one row to the next row. Thus, a gradual change in the Young's modulus can provide a sound bullet of a higher resolution In a further embodiment, static pre-compression of the actuators can be applied to change the velocity of the propagating waves for controlling and/or redirecting the acoustic waves. Particularly, each row of the actuators can be controllably pre-compressed to a pressure such that a first row of the actuators is pre-compressed to a compression different from the compression of at least one other row of actuator, whereby the greater the pre-compression of the actuators, the stiffer the material and/or row of actuators. Young's modulus can be used to measure such stiffness and by precisely pre-compressing each row, the acoustic wave can be redirected to converge at a focal point. For example, pre-compressing the outer rows with a greater pressure and pre-compressing the inner rows with a lesser pressure can create a focal point, resulting in sound bullet.

In another embodiment, some or all of the array of actuators can be replaced with materials having magnetic properties, such as ferromagnetic granular actuators. A magnetic field can be applied around the ferromagnetic array of actuators, thus exerting a force around the array of actuators. Such force can create pre-compressive pressures on the array of actuators.

In an alternative embodiment, each row of the array of actuators can be placed, for example, in an individual row of separate airtight chambers, and the airtight chamber can be placed under a vacuum. In such configuration, a difference in pressure between each of the actuators and the airtight vacuum chamber contributes to pre-compressive forces applied to the array of the actuators.

Figure 7:
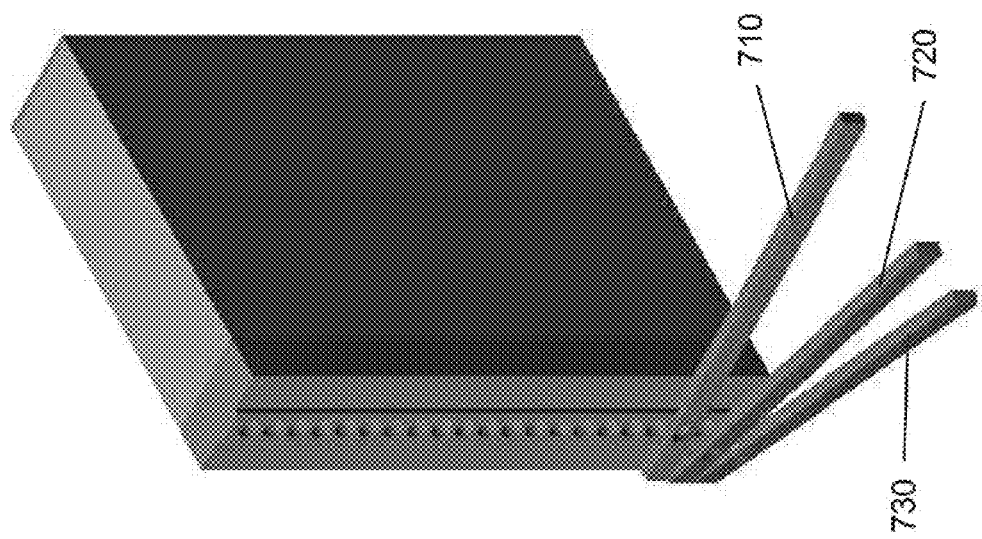
FIG. 7 shows an exemplary two- or three-dimensional system for controlling and/or redirecting acoustic waves or pulses wherein hinged levers are used to apply a pre-compression.
Figure 8A:
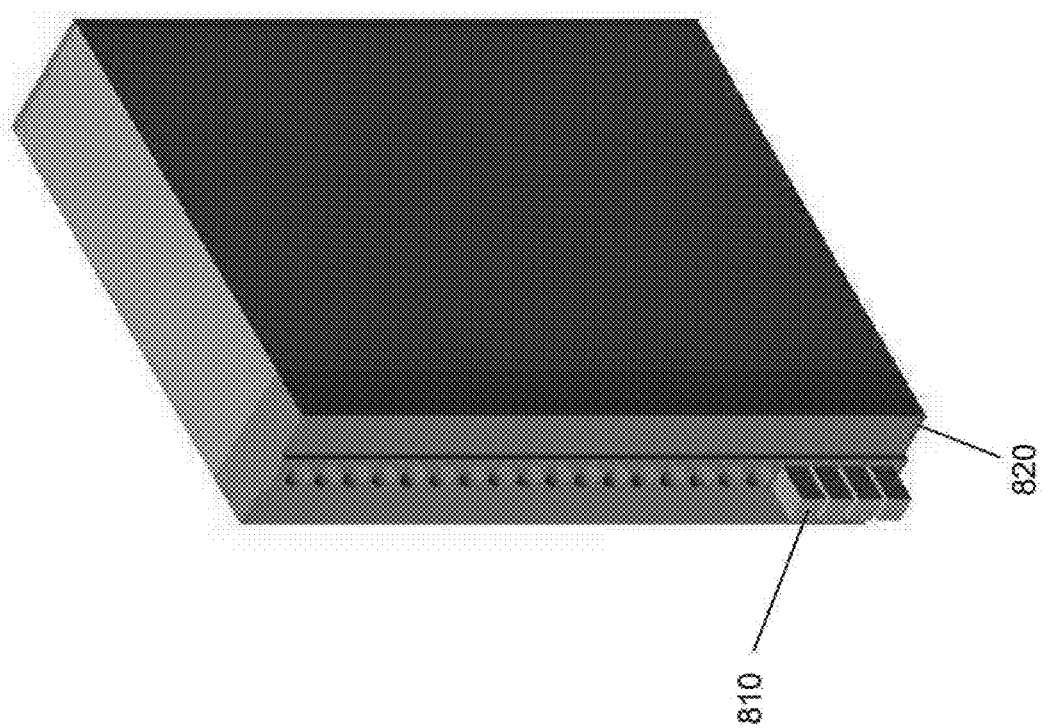
FIG. 8A shows an exemplary two- or three-dimensional system for controlling and/or redirecting acoustic waves or pulses wherein micro- or nano-positioning devices and/or piezoelectric devices are used to apply the pre-compression.
Figure 8B:
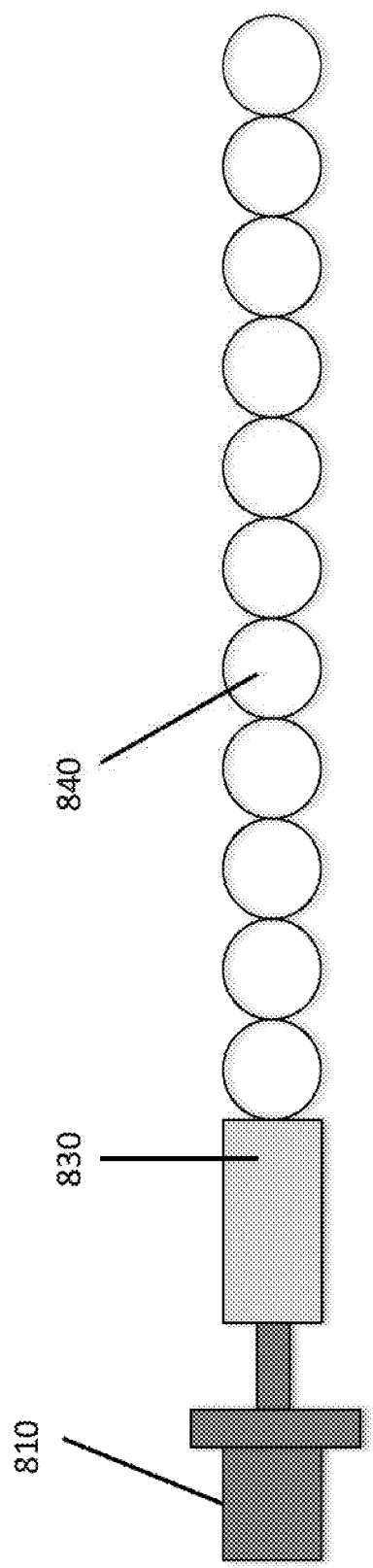
FIG. 8B shows a cross-sectional view of a row of actuators with a micro- or nano-positioning device coupled with a piezoelectric devices.
Figure 8C:
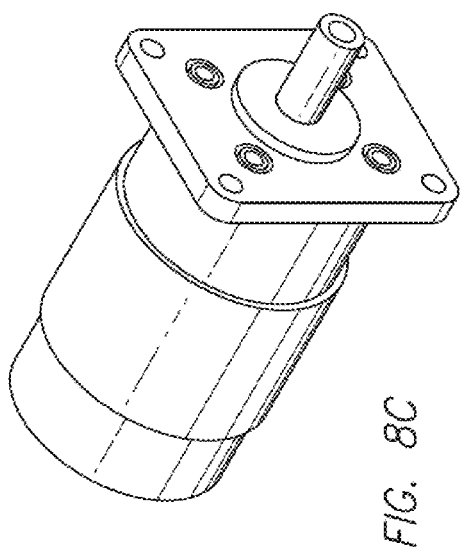
FIGS. 8C-8D show an exemplary micro- or nano-positioning device and a piezoelectric devices, respectively.
Figure 8D:
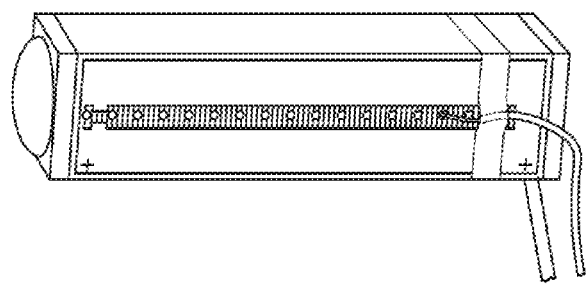

FIG. 7 shows an embodiment of the system for controlling and/or redirecting acoustic waves where hinged levers (710, 720, 730) are provided, hinged to the first end of each row of actuators to apply the pre-compressive pressure to each respective row of the actuators.

FIGS. 8A-8D show yet another embodiment of the system for controlling and/or redirecting acoustic waves according to the disclosure, where micro- or nano-positioning devices (810) are provided, each of them connected with a first end (820) of a respective row of actuators (840). The micro- or nano-positioning devices (810) can be motor controlled such that when adjusted, creates a pre-compressive pressure against the respective row of actuators (840). Additionally, the motor can be can be controlled dynamically by, for example, a computer that can precisely adjust the motor to change to the pre-compressive pressure as desired.

The micro- or nano-positioning devices (810) can be further coupled with static piezoelectric devices (830) connected to each respective row of the actuators (840). Each of the piezoelectric devices (830) can be connected to a voltage source so that a voltage can be applied to the piezoelectric devices (830), thereby causing the micro- or nano-positioning devices (810) to expand, thus applying a pre-compressive pressure to the respective row of the actuators (840) to which it is connected.

FIGS. 9A-9B show yet another embodiment of the present disclosure where a plurality of regulator screws (900) are provided at the first end (910) of the acoustic lens system (920). By way of example and not of limitation, the acoustic lens system (920) can have screw holes (960) at the first end (910) of each row of the actuators (940) such that regulator screws (900) can be inserted into each of the screw holes (960) and configured such that the regulator screws (900) can apply pre-compressive pressure to each respective row of actuators (940) as the regulator screws (900) are screwed in. The regulator screws (900) can have a hole in the center of the screw (970) to insert a device such as a striker (930), to create the impact wave, which propagates through each of the respective rows of actuators (940).

Similarly to the plates (300) shown in FIGS. 3A-3C on the second end (280) of the system, the plates can also be mounted on the first end (270) of the acoustic lens system. In the case where the plates are mounted on the first end (270) of the acoustic lens system, the plates and the screws can be configured as regulator plates and regulator screws such that as the regulator screws are screwed in, the regulator plates apply a pre-compressive pressure to each respective row of the actuators.

Figure 10:
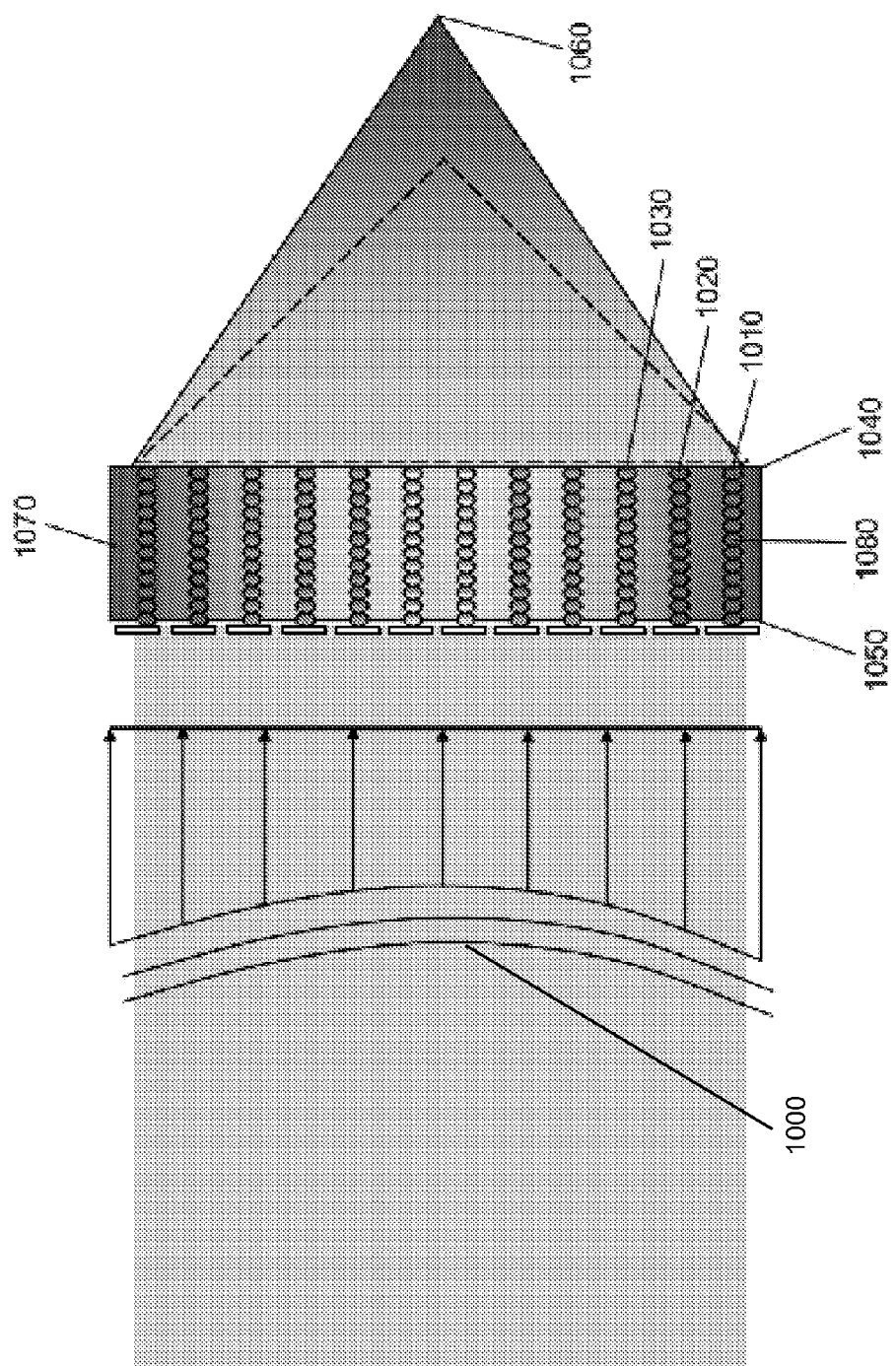
FIG. 10 shows an exemplary two- or three-dimensional system for controlling and/or redirecting acoustic waves or pulses, wherein dynamic force field is used to change the timing of the impact wave.

FIG. 10 shows yet another embodiment where the timing of the impact wave (1000) to the first end (1050) of the two- or three-dimensional acoustic lens system (1070) is changed instead of changing the velocity of the wave propagation through the actuators (1080). The impact wave (1000) applied to a first row (1010) of the actuators (1080) is applied at a different time than when the impact wave (1000) is applied to a second row (1020) of the actuators (1080). By varying the timing of the impact waves (1000), for example, such that impact waves (1000) to the outer rows are applied first and the impact waves (1000) to the inners rows are applied, gradually later, the acoustic waves propagating through the actuators (1080) will arrive at the second end (1040) at times respective to when they arrived at the first end (1050), thus converging at a focal point (1060), and creating a sound bullet.

Figure 11:
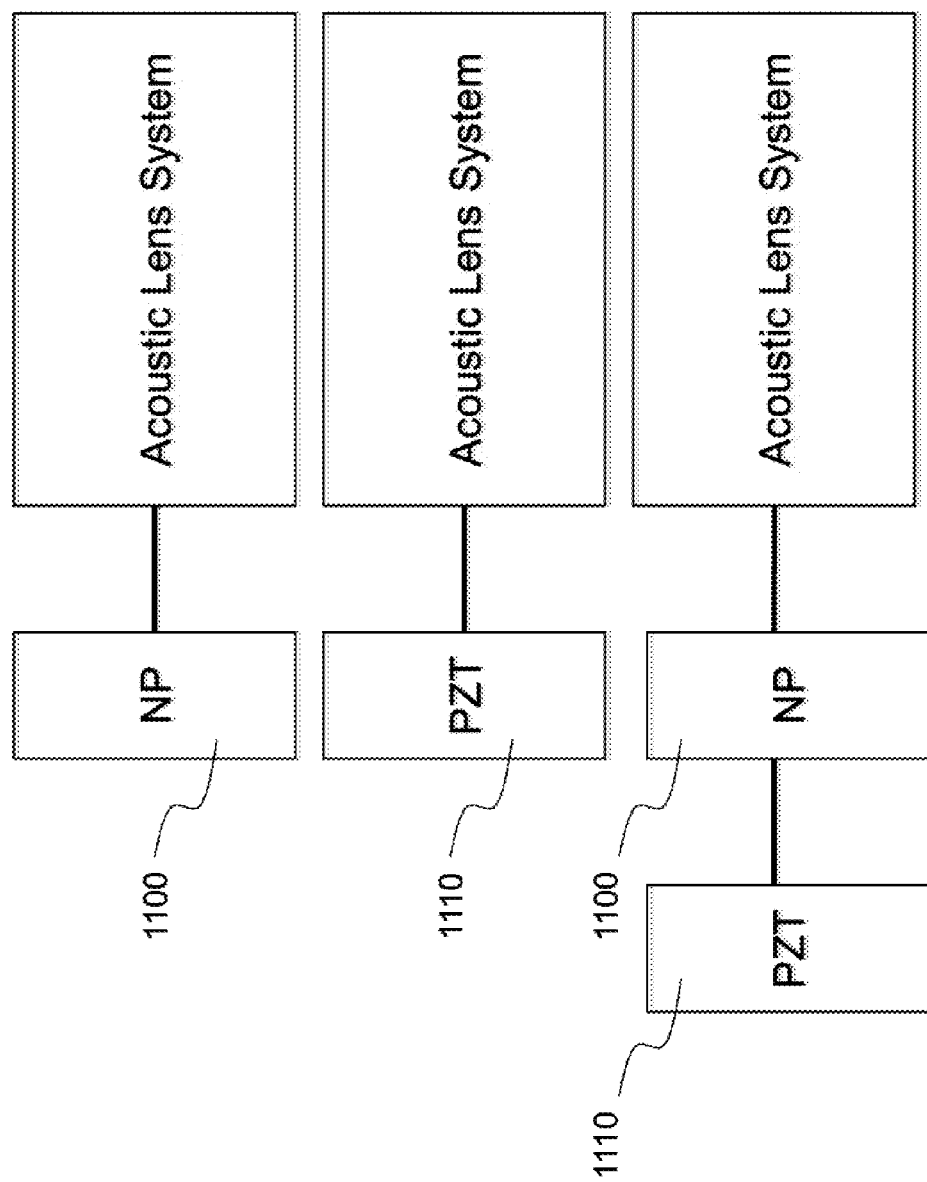
FIG. 11 shows a block diagram of an exemplary system for controlling and/or redirecting acoustic waves or pulses, wherein a combination of one or more techniques can be applied.

Although each embodiment of the present disclosure was described as separate embodiments, any combination of the above methods can be used perform a control and/or redirection of the acoustic waves with further precision as shown in FIG. 11. For example, an exemplary acoustic lens system (1120) can have actuators made of different material, further comprising motor controlled nano-positioners (1100) and piezoelectric devices (1110) applying pre-compression.

Figure 12:
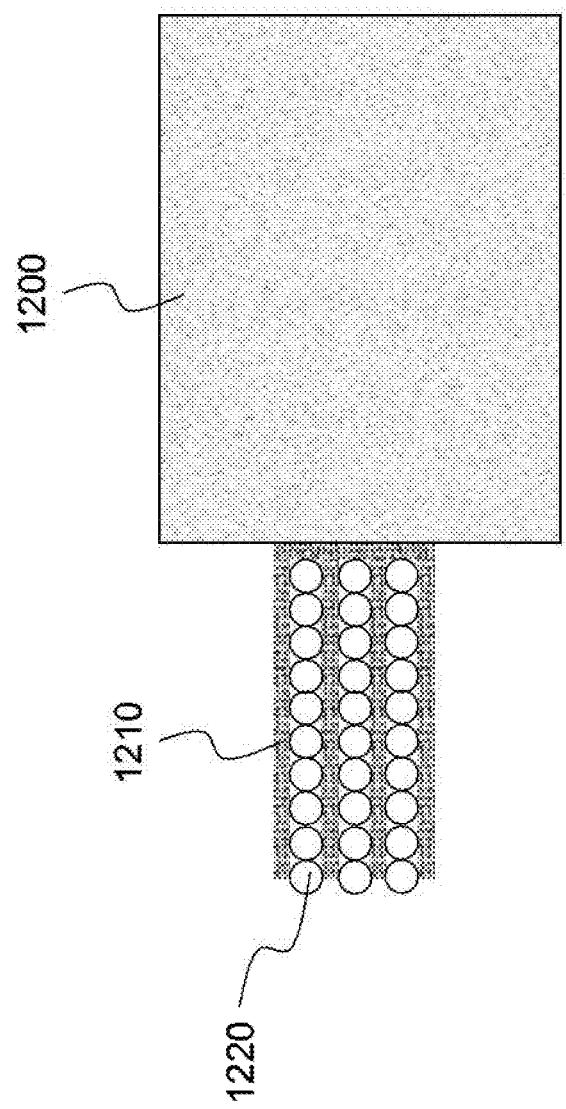
FIG. 12 shows a schematic diagram of a system for controlling and/or redirecting acoustic waves or pulses, wherein the actuators protrude from the system.
Figure 13:
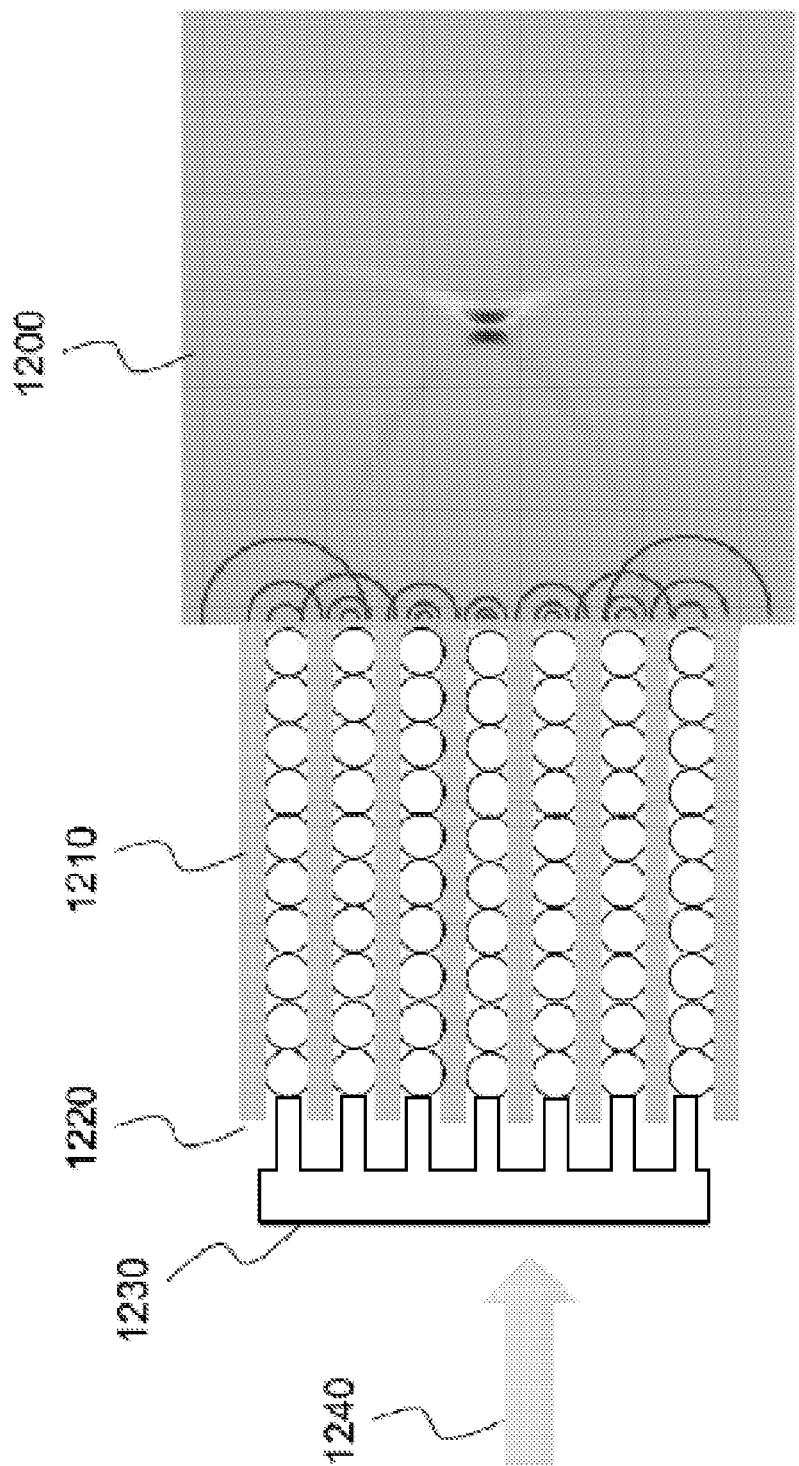
FIG. 13 shows a schematic diagram of a system for controlling and/or redirecting acoustic waves or pulses, wherein the actuators are recessed within the system.

FIGS. 12-13 show the acoustic lens system (1210) configured to propagate the sound bullet to a host medium (1200) (e.g., water, air, solid). In FIG. 12, the first end (1220) of the row of the actuators protrude from the container or the matrix such that when an impact wave is applied to the first end (1220), the actuators will absorb a significant portion of the impact wave. However, the system in FIG. 13 shows the first end (1220) of the row of actuators to be recessed within the container or the matrix. In such case, an extension element (1230) is connected with the first end (1220) to ensure the impact wave is fully absorbed by the actuators instead of being absorbed by the matrix.

The examples set forth above are provided to give those of ordinary skill in the art a complete disclosure and description of the acoustic lens system and methods to control and/or redirect acoustic waves or pulses in the present disclosure, and are not intended to limit the scope of what the inventors regard as their disclosure. Modifications of the above-described modes for carrying out the disclosure may be used by persons of skill in the art, and are intended to be within the scope of the following claims. All patents and publications mentioned in the specification may be indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

A number of embodiments of the disclosure have been described. Nevertheless, it will be understood that various modifications may be made without departing from the spirit and scope of the present disclosure. Accordingly, other embodiments are within the scope of the following claims.

References

[1] Khatri, D., P. Rizzo, and C. Daraio. *Highly Nonlinear Waves' Sensor Technology for Highway Infrastructures.* in *SPIE Smart Structures/NDE, 15th annual international symposium.* 2008. San Diego, Calif.
[2] Wade, G, *Acoustic Imaging,* 1976, NY: Plenum Press
[3] Lele, P. P., *Hyperthermia by ultrasound* in Proc. Int. Symp. on Cancer Therapy by Hyperthermia and Radiation. 1975, pp. 168-176.
[4] Ochletree, K. B., Benkesser, P. J., Frizzell, L. A, and Cain, C. A., *An ultrasonic phased array applicator for hyperthermia,* IEEE Trans. Son. Ultrasun. vol. SU-31. pp. 526-531, 1984.

[5] Cain, C. and Umemura, S. *Concentric-ring and sector vortex phased-array applicators for ultrasound hyperthermia*, IEEE Trans. MTT, Vol. MTT-34, no. 5. pp. 542-55

[6] Turnbull, D. H. and Foster F. S., *Beam steering with pulsed two-dimensional transducer arrays*, IEEE Trans. Ultrason. Ferroelec. Freq. Contr., 38, no. 6, pp. 320-333, 1991

[7] Ebbini, E. F. and Cain C. A., *Multiple-focus Ultrasound Phased-Array Pattern Synthesis: Optimal Driving Signal Distributions for Hyperthermia*, IEEE Trans. Ultrason. Femelec. Freq. Contr. 36 NO. 5, 540-548, 1989

[8] Lalonde, R, Worthington, A. and Hunt, J. W., Field Conjugate acoustic lenses for ultrasound hyperthermia, 1342-1991 ULTRASONICS SYMPOSIUM

[9] Lalonde, R and Hunt, J. W, *Variable Frequency Field Conjugate Lenses for Ultrasound Hyperthermia*, IEEE Trans.Ultrason.Ferroelectr.Freq.Contr.42825-31

[10] G. R. ter Haar, *Ultrasound Med. Biol.* 21, 1089 (1995). G. ter Haar, *Semin. Laparosc. Surg.* 8, 77 (2001). S. Vaezy, M. Andrew, P. Kaczkowski, L. Crum, *Annu. Rev. Biomed. Eng.* 3, 375 (2001)., also Physics Today References February 2000, page 29; March 1997, page 34

[11] Holt, R. G., Roy, R. A, Edson, P. A. Yang, X, Bubbles and HIFU: *the good, the bad and the ugly*, in Andrew, M. A, Crum, L. A, Vaezy. S, *Proceedings of the 2nd International Symposium on Therapeutic Ultrasound,* 2002, pp. 120-131

[12] Clement, G. T., *Perspectives in clinical use of high-intensity focused ultrasound* Ultrasonics 42 (2004)1087-1093

[13] Nesterenko, V. F., *Propagation of nonlinear compression pulses in granular media*. Journal of Applied Mechanics and Technical Physics Zhurnal Prikladnoi Mekhaniki i Tehknicheskoi Fiziki, 1983. 24(51 vol. 24, no. 5): p. 733-431136-48.

[14] Porter, M. A., et al., *Highly nonlinear solitary waves in periodic dimer granular chains*. Physical Review E, 2008. 77: p. 015601.

[15] B. D. V. Veen and K. M. Buckley. *Beamforming: A versatile approach to spatial filtering*. IEEE ASSP Magazine, pages 4-24, April 1988.

[16] H. L. Van Trees, *Optimum Array Processing*, Wiley, NY, 2002, and M. C. Sullivan, *Practical Array Processing*, McGraw-Hill, 2009

[17] Daraio, C., et al., *Pulse mitigation by a composite discrete medium*. Journal De Physique Iv, 2006. 134: p. 473-479.

[18] Daraio, C., et al., *Tunability of solitary wave properties in one-dimensional strongly nonlinear phononic crystals*. Physical Review E, 2006. 73(2).

[19] Daraio, C., et al., *Energy trapping and shock disintegration in a composite granular medium*. Physical Review Letters, 2006. 96(5).

[20] Job, S., et al., *How Hertzian solitary waves interact with boundaries in a 1D granular medium*. Physical Review Letters, 2005. 94(17).

[21] Nesterenko, V. F., et al., *Anomalous wave reflection at the interface of two strongly nonlinear granular media*. Physical Review Letters, 2005. 95(15).

[22] Porter, M. A., et al., *Highly Nonlinear Solitary Waves in Heterogeneous Periodic Granular Media*. Physica D, 2009: p. (in press).

[23] Remoissenet, M., *Waves Called Solitons (Concepts and Experiments)*. 3rd revised and enlarged edition ed, ed. Springer-Verlag. 1999, Berlin.

[24] Sen, S., Hong, J., Bang, J., Avalosa, E., Doney, R., *Solitary waves in the granular chain*. Physics Reports, 2008. 462: p. 21-66.

The invention claimed is:

1. A system for controlling and/or redirecting acoustic waves or pulses, the system comprising:
a two-dimensional or three-dimensional array of rows of actuators, each row comprising a plurality of independently tuned nonlinear actuators, wherein each nonlinear actuator comprises nonlinear material configured for propagating a highly nonlinear acoustic wave and the actuators being made of different materials such that a first row of the array of actuators is made of a first material and at least a second row of the array of actuators is made of a second material different from the first material.

2. The system of claim 1, wherein each row of actuators comprises nonlinear actuators, the nonlinear actuators being granular particles arranged in a chained configuration.

3. The system of claim 2, wherein the granular particles are selected from the group consisting of: spherical granular particles, elliptical granular particles, and conical granular particles.

4. The system of claim 1, wherein the first and second materials are selected from the group consisting of: rubber, PTFE, glass, brass, bronze, ceramic materials, steel and alloys.

5. The system of claim 1, wherein the two-dimensional or three-dimensional array of rows comprises inner row regions of the array and outer row regions of the array, the materials for the outer row regions of the array made of heavier material than the material for inner row regions.

6. The system of claim 1, wherein the two-dimensional or three-dimensional array of rows comprises inner row regions of the array and outer row regions of the array, the materials for the outer row regions of the array made of stiffer material than the material for inner row regions, the stiffness of the material being determined by Young's modulus of stiffness.

7. The system of claim 1, wherein the two-dimensional or three-dimensional array of rows comprises inner row regions of the array and outer row regions of the array, the materials for the inner row regions of the array made of heavier material than the material for outer row regions.

8. The system of claim 1, wherein the two-dimensional or three-dimensional array of rows comprises inner row regions of the array and outer row regions of the array, the materials for the inner row regions of the array made of stiffer material than the material for outer row regions, the stiffness of the material being determined by Young's modulus of stiffness.

9. The system of claim 1, wherein a Young's modulus of stiffness of a first row of the actuators varies from a Young's modulus of stiffness of an adjacent row of the actuators.

10. A system for controlling and/or redirecting acoustic waves or pulses, the system comprising:
a two-dimensional or three-dimensional array of rows of actuators, each row comprising a plurality of independently tuned nonlinear actuators, wherein each nonlinear actuator comprises nonlinear material configured for propagating a highly nonlinear acoustic wave; and
a plurality of regulator screws, each regulator screw associated with a first end of a respective row of actuators, the plurality of regulator screws configured to controllably precompress each respective row of actuators to which the regulator screws are connected with, such that a first row of the actuators is pre-compressed to a compression different from the compression of at least one other row of the actuators.

11. A system for controlling and/or redirecting acoustic waves or pulses, the system comprising:
a two-dimensional or three-dimensional array of rows of actuators, each row comprising a plurality of independently tuned nonlinear actuators, wherein each nonlinear actuator comprises nonlinear material configured for propagating a highly nonlinear acoustic wave; and a plurality of hinged levers, each hinged lever connected with a first end of a respective row of actuators, wherein the plurality of hinged levers are configured to controllably pre-compress each respective row of actuators to which the hinged levers are connected, such that a first row of the actuators is pre-compressed to a compression different from the compression of at least one other row of the actuators.

12. A system for controlling and/or redirecting acoustic waves or pulses, the system comprising:

a two-dimensional or three-dimensional array of rows of actuators, each row comprising a plurality of independently tuned nonlinear actuators, wherein each nonlinear actuator comprises nonlinear material configured for propagating a highly nonlinear acoustic wave; and a plurality of micro- or nano-positioning devices, each micro- or nano-positioning device connected with a first end of a respective row of actuators, wherein the plurality of micro- or nano-positioning devices are configured to controllably pre-compress each respective row of actuators to which the micro- or nano-positioning devices are connected, such that a first row of the actuators is pre-compressed to a compression different from the compression of at least one other row of the actuators.

13. The system of claim 12, further comprising a plurality of piezoelectric devices, each piezoelectric device coupled with a respective micro- or nanopositioning device.

14. The system of claim 13, wherein the micro- or nano-positioning devices comprise motor controllable micro- or nano-positioning devices.

15. The system of claim 14, wherein the motor controllable micro- or nano-positioning devices comprise computer-controllable micro- or nano-positioning devices.

16. A system for controlling and/or redirecting acoustic waves or pulses, the system comprising:

a two-dimensional or three-dimensional array of rows of actuators, each row comprising a plurality of independently tuned nonlinear actuators, wherein each nonlinear actuator comprises nonlinear material configured for propagating a highly nonlinear acoustic wave; and a plurality of piezoelectric devices, each piezoelectric device connected with a first end of a respective row of actuators.

17. The system of any one of claim 1, 10, 11, or 12, wherein the acoustic waves or pulses are a single acoustic wave or pulse and/or trains of acoustic waves or pulses.

18. The system of any one of claim 1, 10, 11, or 12, wherein the nonlinear actuators are ferromagnetic granular particles.

19. The system of any one of claim 1, 10, 11, or 12, wherein each row of the nonlinear actuators are arranged in a vacuum chamber.

20. The system of any one of claim 1, 10, 11, or 12, wherein the nonlinear actuators are arranged in a matrix, the matrix being a polymer material with a Young's modulus smaller than the Young's modulus of the actuators.

21. The system of any one of claim 1, 10, 11, or 12, wherein the array of the rows of nonlinear actuators is separated from adjacent rows with a plurality of shim stocks coated with non-stick material.

22. The system of any one of claim 1, 10, 11, or 12, wherein the nonlinear actuators at a first end of each row protrude from the system such that the protrusion of the nonlinear actuators is configured to absorb the acoustic waves or pulses.

23. The system of any one of claim 1, 10, 11, or 12, wherein the nonlinear actuators at a first end of each row are recessed from the system, further comprising an extension element connected with the recessed nonlinear actuators such that the extension element absorbs the acoustic waves or pulses such that the acoustic waves or pulses propagate from the extension element to the nonlinear actuators.

24. The system of any one of claim 1, 10, 11, or 12, further comprising a plurality of plates connected to a first end of the array of rows of actuators, the plurality of the plates adapted to contain the nonlinear actuators, wherein a thickness of the plurality of plates is adapted to enable the acoustic waves or pulses to propagate through the plurality of the plates.

25. A method of controlling and/or redirecting acoustic waves or pulses, the method comprising:

providing a two-dimensional or three-dimensional array of rows of actuators, each row comprising a plurality of independently tuned nonlinear actuators, wherein each nonlinear actuator comprises nonlinear material configured for propagating a highly nonlinear acoustic wave;

providing a plurality of regulator screws, each regulator screw associated with a first end of a respective row of actuators; and pre-compressing each row of the actuators such that a first row of the actuators is precompressed to a compression different from at least one other row of the actuators, the precompressing being performed by screwing in or screwing out the plurality of the regulator screws, wherein differences in compression of each of the rows of actuators control and/or redirect the acoustic waves or pulses.

26. A method of controlling and/or redirecting acoustic waves or pulses, the method comprising:

providing a two-dimensional or three-dimensional array of rows of actuators, each row comprising a plurality of independently tuned nonlinear actuators, wherein each nonlinear actuator comprises nonlinear material configured for propagating a highly nonlinear acoustic wave;

providing a plurality of hinged levers, each hinged lever connected with a first end of a respective row of actuators; and pre-compressing each row of the actuators such that a first row of the actuators is precompressed with the hinged lever to a compression different from at least one other row of the actuators, wherein differences in compression of each of the rows of actuators control and/or redirect the acoustic waves or pulses.

27. A method of controlling and/or redirecting acoustic waves or pulses, the method comprising:

providing the system according to claim 13; and pre-compressing each row of the actuators with the piezoelectric devices, applying compressive forces controlled by a motor controller, such that the first row of the actuators is pre-compressed to a compression different from at least one other row of the actuators, wherein differences in compression of each of the rows of actuators control and/or redirect the acoustic waves or pulses.

28. A method of controlling and/or redirection acoustic waves or pulses, the method comprising:

providing a two-dimensional or three-dimensional array of rows of actuators, each row comprising a plurality of independently tuned nonlinear actuators, wherein each nonlinear actuator comprises nonlinear material configured for propagating a highly nonlinear acoustic wave; and providing acoustic waves or pulses to a first end of the rows of the actuators, the input acoustic waves or pulses propagating to a first row of the actuators at a different time from the acoustic waves or pulses propagating to at least one other row of the actuators, thereby controlling and/or redirecting the acoustic waves or pulses exiting from a second end of the rows of the actuators.

29. The method of claim 28, wherein differences in the time of the acoustic waves or pulses propagating to the rows of actuators forms a convex waveform, thereby focusing the acoustic waves and/or pulses exiting from the second end of the rows of the actuators.

* * * * *